United States Patent [19]

Cohen et al.

[11] Patent Number: 5,304,488
[45] Date of Patent: Apr. 19, 1994

[54] INSTALLATION FOR OBTAINING PLASMIDS AND COSMIDS

[75] Inventors: Daniel Cohen, Saint-Mande; Frédéric Dufau, La-Celle-Saint-Cloud; Jean Hache, Voisins-le-Bretonneux, all of France

[73] Assignee: Bertin & Cie, Plaisir, France

[21] Appl. No.: 975,815

[22] Filed: Nov. 13, 1992

Related U.S. Application Data

[62] Division of Ser. No. 477,806, Mar. 19, 1990, abandoned.

[30] Foreign Application Priority Data

Jun. 21, 1988 [FR] France .................. 88 08306

[51] Int. Cl.⁵ .................. C12M 1/12; C12M 1/34; C12M 1/18; C12M 1/14
[52] U.S. Cl. .................. 435/291; 435/300; 435/310; 435/311; 435/287; 204/299 R
[58] Field of Search ............ 204/299 R, 182.8, 180.1; 435/287, 290, 291, 311, 299, 300, 310; 436/516, 515

[56] References Cited

U.S. PATENT DOCUMENTS

| | | | |
|---|---|---|---|
| 3,964,992 | 6/1976 | Krotz | 204/299 R |
| 4,716,101 | 12/1987 | Thompson et al. | 204/299 R |
| 4,735,697 | 4/1988 | Burton | 204/299 R |
| 4,818,701 | 4/1989 | Littlehales | 435/287 |
| 4,892,638 | 1/1990 | Watanabe et al. | 204/299 R |
| 5,139,637 | 8/1992 | MacConnell | 204/299 R |
| 5,188,963 | 2/1993 | Stapleton | 435/299 |

OTHER PUBLICATIONS

McClelland et al., "Restriction Endonucleases for Pulsed Field Mapping of Bacterial Genomes", Nucleic Acids Research, vol. 15, No. 15, pp. 5985–6005, 1987.
Ratlios et al., Curr. Sci., 58(22), 1235–39, 1989 Chemical Abstracts, vol. 112, No. 9, 73248C, 1990.
Kinashi et al., "Giant Linear Plasmids in Streptomyces Which Code for Antibiotic Biosynthesis Genes", Nature, vol. 328, pp. 454–456, Jul. 30, 1987.

Primary Examiner—James C. Housel
Assistant Examiner—T. A. Trembley
Attorney, Agent, or Firm—Bell, Seltzer, Park & Gibson

[57] ABSTRACT

A process of separating plasmids and cosmids from bacterial cells in which they are contained, comprising adding cultured bacterial cells separated from a culture medium to an inclusion gel-forming substance; lysing the bacterial cells; solubilizing the thus lysed bacterial cells; solidifying the inclusion gel-forming substance to form a gel either before or after the step of solubilizing; and applying an electric field to the thus formed gel sufficient to cause electrophoretic migration of the plasmids and cosmids and isolation of the plasmids and cosmids. Also disclosed is a device for carrying out the process.

12 Claims, 3 Drawing Sheets

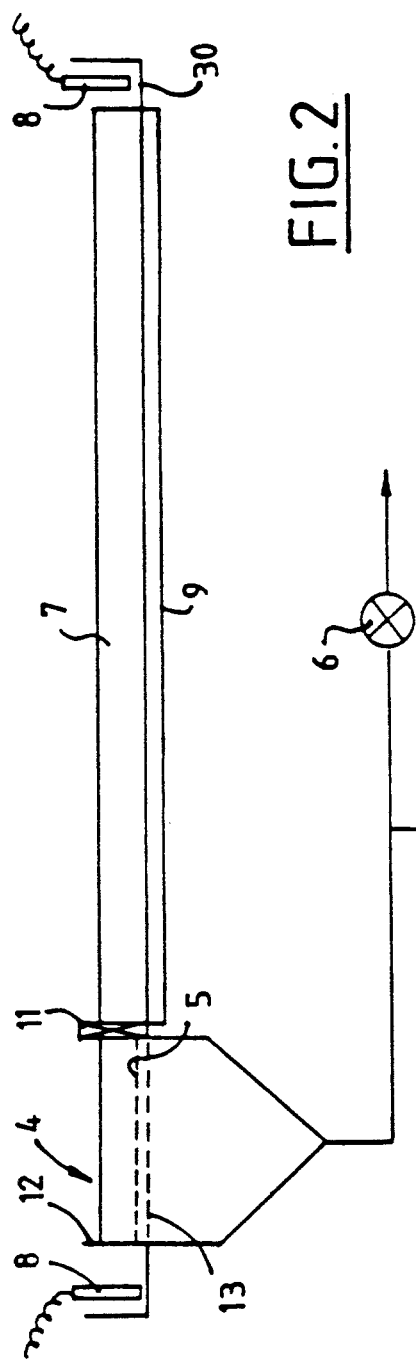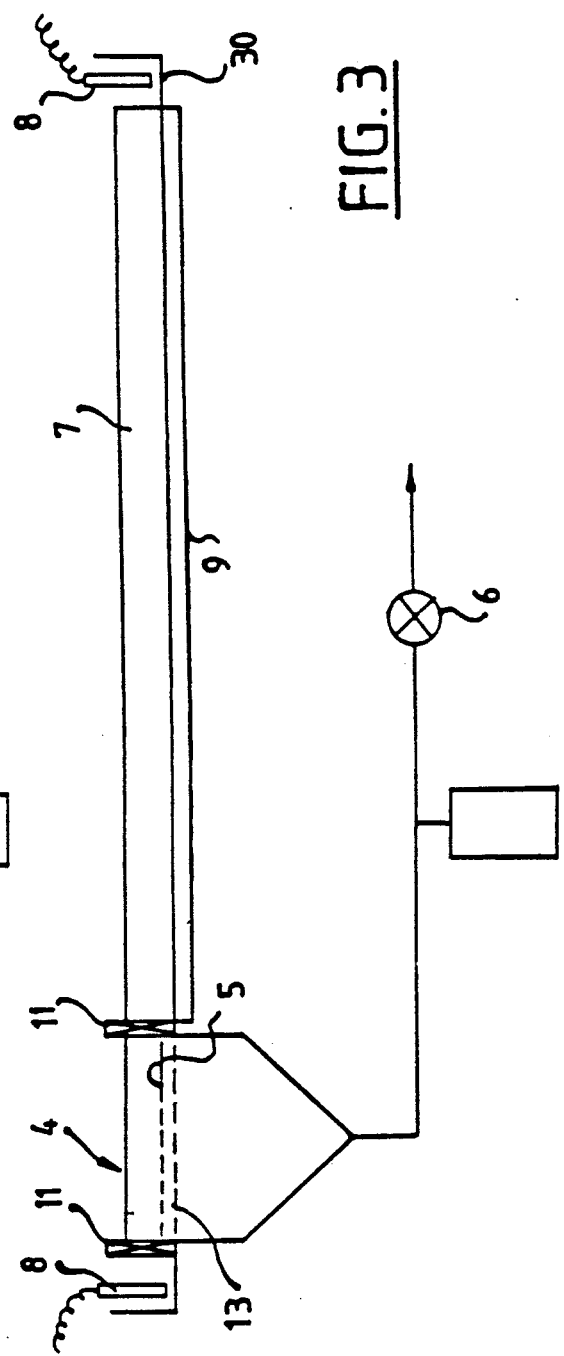

INSTALLATION FOR OBTAINING PLASMIDS AND COSMIDS

This application is a divisional of application Ser. No. 07/477,806, filed Mar. 19, 1990, now abandoned.

The present invention relates to a process and to an installation for obtaining whole plasmids and cosmids.

Plasmids are extra-chromosomal, circular, double strand DNA molecules, which are found in many bacterial strains. Their size varies from 1 kbase to 200-300 kbases and is much smaller than that of chromosomes, for example.

BACKGROUND OF THE INVENTION

In the prior art, it is known to separate plasmids present in various bacteria, by centrifugation. The centrifugation of bacterial cells, only enables a low yield of plasmids to be obtained, of the order of 20%. Now, plasmids have, at the present time, many uses, particularly as hybridization probes or as vectors. As the demand for plasmids is becoming greater and greater, the possibility of obtaining whole plasmids with very high yield, is therefore of positive practical interest to the industries concerned.

SUMMARY OF THE INVENTION

Applicants have, consequently, set themselves the target of providing a specific process for obtaining whole plasmids and cosmids which does not have the drawbacks of the processes proposed in the prior art, particularly in that it enables a yield of close to 100% of whole plasmids and cosmids, to be obtained and is easy to put into practice and inexpensive, and an automatized installation for performing this process.

It is an object of the present invention to provide a process for obtaining whole plasmids and cosmids present in bacterial cells, cultivated in a suitable medium, characterized in that in the course of a first step said cells are separated from their culture medium, in that in the course of a second step, said cells are included in a suitable gel, their walls being then lysed by contacting with a suitable reagent, and then said included cells are solubilized by means by at least one suitable reagent, and that in the course of a third step, said solubilized cells, included in said gel, are subjected to a suitable electrical field, causing their electrophoretic migration, which specifically isolates the whole plasmids and cosmids present in said cells.

The lysis of the cell walls is performed in known and conventional manner by means of lysozyme.

According to one embodiment of the process, the lysis of the cell walls is performed before solidification of the inclusion gel.

According to another embodiment of the process, the lysis of the cell walls is performed after solidification of the inclusion gel.

According to another embodiment, the inclusion gel is agarose at a concentration comprised between 0.1% and 5%, without these indications having, of course, any limiting character whatever.

According to another embodiment of the process, the solubilization is performed chemically or biochemically by means of a reagent selected from the group which comprises suitable proteolytic enzymes and detergent solvents of lipids.

In the solubilization process, the proteolytic enzyme which may be used, may be proteinase K, pronase, or any other suitable protease; in said process, the following detergent may be mentioned particularly sodium dodecyl sulfate (SDS); the proteinase K-SDS association, for example, is very advantageous.

According to an advantageous arrangement of this embodiment, said solubilization is performed before solidification of the gel.

According to another advantageous arrangement of this embodiment, said solubilization is performed after solidification of the gel.

According to another embodiment of the process, the duration of electrophoretic migration is comprised between two and twelve hours.

According to one advantageous arrangement of this embodiment, the electrophoretic migration is performed in known manner in pulsed fields.

In such an embodiment, there is provided, of course, cooling of the migration system by heat regulating means, which serve advantageously also, in case of need, during the solubilization of the cells, when this is necessary.

The present invention also relates to an installation for obtaining whole plasmids and cosmids present in bacterial cells, characterized in that it comprises at least one means of separating the cells from their culture medium, at least one treatment chamber, at least one electrophoresis gel as an electrophoretic migration medium, adjacent to, and associated with said treatment chamber, at least one means for applying an electric field which causes electrophoretic migration, removable and/or retractable means for placing said electrophoresis gel in communication with said treatment chamber and an automatization microprocessor for the sequential control of said separating means, said communication means and said means for applying an electric field.

According to an advantageous embodiment, the installation comprises in addition at least one culture chamber for said cells and a transfer means for said cells from the culture chamber into the treatment chamber, said transfer means comprising transfer tubes connected on the one hand to the culture chamber, and on the other hand to the treatment chamber, and a differential pressure device between said culture chamber and said treatment chamber.

According to one arrangement of this embodiment, said device is a peristaltic pump.

According to another arrangement of this embodiment, said device is a pressurizing means connected to the culture chamber.

According to yet another arrangement of this embodiment, said device is a vacuum pump connected to the treatment chamber.

According to another embodiment of the installation, the treatment chamber is advantageously a tank, whose bottom comprises separating means constituted by a membrane of suitable porosity for the separation of molecules of molecular weight higher than 80 kDa.

In such an embodiment, the tank comprises three fixed walls of which one, adjacent to one of the electrodes of the electric field applying means, is a dialysis membrane and the removable means for placing in communication the electrophoresis gel with the treatment tank are then, most simply, a rule materializing the fourth wall of said tank, placed in position for the flow of the gel in the treatment tank.

In a modification, the tank is limited by four simultaneously removable rules, placed in position for the flow of the gel and one of the electrodes of the electric field applying means is then, if necessary, adjacent to a dialysis membrane.

In a preferred embodiment, the vacuum pump ensuring the transfer of the cells from the culture chamber to said treatment tank supplies simultaneously reduced pressure for sucking the culture medium through said membrane.

The invention comprises advantageously a detector locating the site of the whole plasmids and cosmids after said electrophoretic migration.

There is thus obtained, by the combination of means of the present invention, a rapid automatized separation of whole plasmids and cosmids, that is easy to put into practice.

BRIEF DESCRIPTION OF THE DRAWINGS

Besides the foregoing features, the invention comprises yet other features, which will emerge from the description which follows, which refers to examples of the process according to the invention and to a detailed description of the installation with reference to the accompanying drawing, in which:

FIG. 2 shows a very diagramatic view in longitudinal section, illustrating an embodiment of a portion of the installation; and FIG. 3 shows a very diagramatic view in longitudinal section, illustrating another embodiment of a portion of the installation.

It must be well understood, however, that this drawing and the corresponding descriptive portions, as well as the examples, are given purely by way of illustration of the invention, of which they do not in any way constitute a limitation.

DETAILED DESCRIPTION OF THE PREFERRED EMBODIMENT

Figure 1:
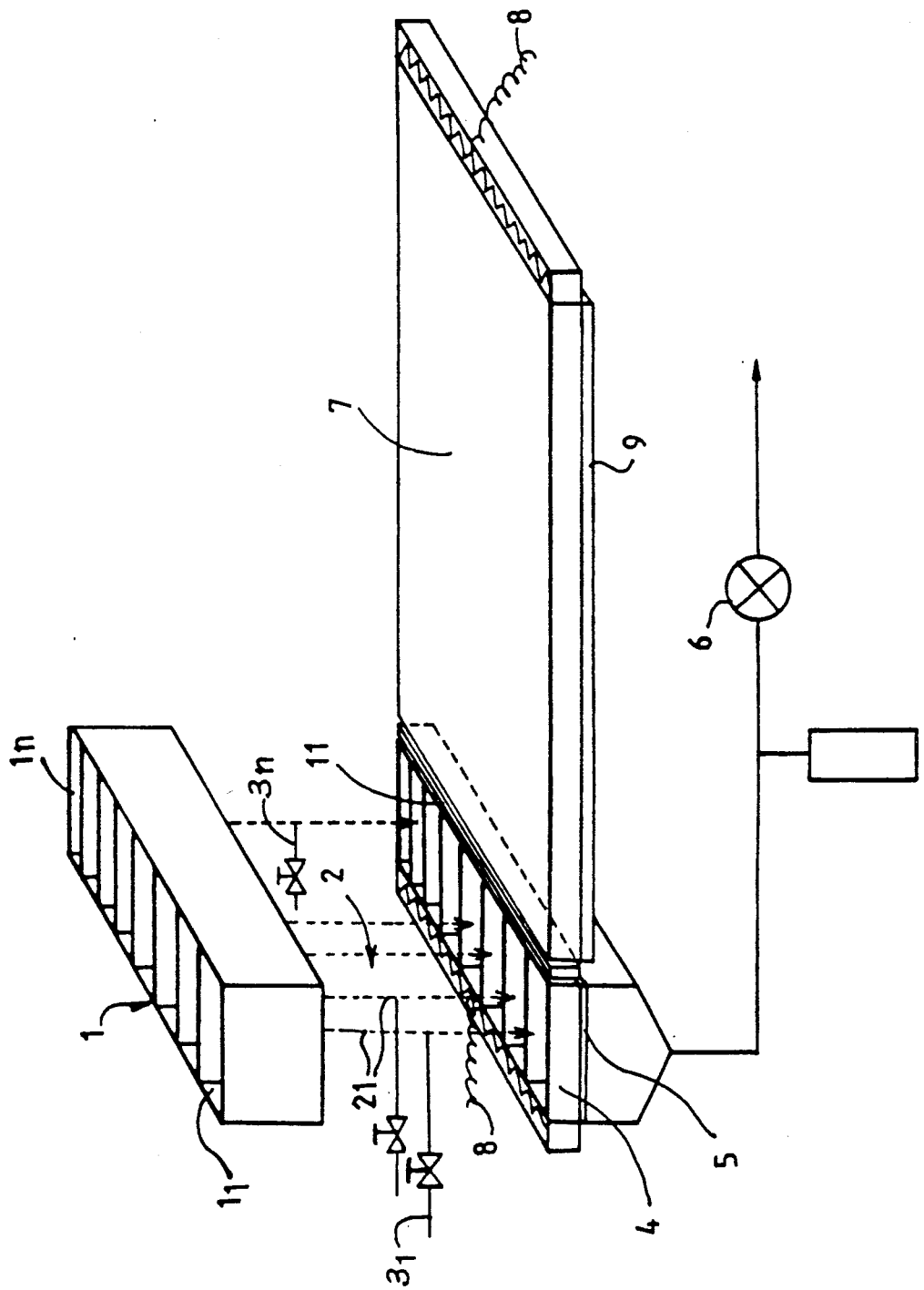
FIG. 1 shows a diagramatic view illustrating the process of the invention.

The process according to the invention, for obtaining plasmids and cosmids is illustrated in FIG. 1. Plasmid or cosmid host bacteria are selected and cultivated suitably, in a cell culture chamber 1 comprising a certain number of compartments $1_1$ and $1_n$ enabling the growth in parallel of different bacterial cells accommodating different plasmids or cosmids. After having obtained a suitable cell concentration, said cultures are transferred into the treatment tank 4 through transfer means 2, which in the embodiment shown are constituted by tubes 21 and a vacuum pump 6, the treatment tank 4 then being provided with a cover (not shown). The determination of the cell concentration may be performed in different ways and particularly but without limitation, by colorimetric measurement. The cells are then separated from their culture medium, the separating means being represented by the bottom of the treatment tank 4 which is a suitable membrane 5, for example, and without limitation, an ultra-filtration membrane of "Teflon" (a registered trade mark of Dupont de Nemours Company) which retains especially elements of more than 80 kDa.

The vacuum pump 6 ensures at the same time transfer of the cells from the culture chamber 1 to the treatment tank 4 and provides also the reduced pressure for sucking and removing culture medium through said membrane 5. A series of pipettes $3_1$ to $3_n$ connected to the tubes 21 enables the introduction of reagents and particularly of agarose, which is then introduced hot, at a temperature of about 65° C. and enables the inclusion of said cells; the cell walls are then lysed, for example, by means of lysozyme; the latter is kept in contact with said cells for 5 to 10 minutes. This lysis may be performed indifferently before solidification of the inclusion gel, at a temperature of the order of 37° C. or after solidification of the inclusion gel.

The cells are then solubilized, and the solubilization can be performed indifferently before or after solidification of the inclusion gel, by means of a suitable enzyme, possibly associated with a detergent, for example, but without limitation proteinase K and SDS.

After solubilization, the electrophoretic migration, in pulsed or unpulsed fields, is performed; the treatment tank 4 is then connected to the layer of electrophoresis gel 7 by withdrawing the movable wall 11 which in the embodiment shown is one of the removable walls of the treatment tank 4, and the space between the gel containing the treated cells and the electrophoresis gel 7 is filled by electrophoresis gel. The wall 12 of the treatment tank 4 is a dialysis membrane. Electrodes 8 enable the production of an electric field suitable for the desired electrophoretic migration.

The treatment tank 4 and the layer of electrophoresis gel 7 are placed in a container 30, in which are located the electrophoresis buffer and the electrodes 8. A detector 9 enables the site of migration of the plasmids and of the cosmids to be located.

The process according to the invention enables within a short time, comprised between two and twelve hours, the obtaining specifically of the plasmids and the cosmids, the latter migrating on to the gel whereas, on the one hand, the chromosomes remain at the level of the deposit and, on the other hand, the solubilization products (peptides, etc.) are not retained by the gel.

FIG. 2 shows a very diagramatic view in longitudinal section, of an embodiment of a portion of the installation and comprises a treatment tank 4 including a removable wall 11 and three fixed walls of which that which is adjacent to the electrode 8 being close to the treatment tank 4, is a dialysis membrane 12.

The receptacle 30 of the treatment tank 4 and of the electrophoresis gel 7 comprises:

a suitable support 13, on which is located the bottom of the treatment tank 4, in the form of a suitable membrane 5, for example and without limitation, an ultra-filtration membrane of "Teflon" which retains particularly elements of more than 80 kDa; and the means for applying the electric field, represented by the electrodes 8.

With the separating means 5 of the cells from their culture medium, is associated the vacuum pump 6.

A detector 9 enables the location of the migration site of the plasmids and the cosmids.

FIG. 3 shows a very diagramatic view in longitudinal section, of another embodiment of a portion of the installation and comprises a treatment tank 4 including two removable walls 11 and two fixed walls.

Receptacle 30 of the treatment tank 4 and of the electrophoresis gel 7 comprises:

a suitable support 13, on which is located the bottom of the treatment tank 4, in the form of a suitable membrane 5, for example and without limitation, an ultra-filtration membrane of "Teflon" which retains particularly elements of more than 80 kDa; and the means for applying the electric field, represented by the electrodes 8.

With the separating means 5 of the cells from their culture medium, is associated the vacuum pump 6.

A detector 9 enables the location of the migration site of the plasmids and the cosmids.

Such installations enable the practicing of the process for obtaining plasmids and cosmids according to the invention.

EXAMPLE 1

Figure 4:
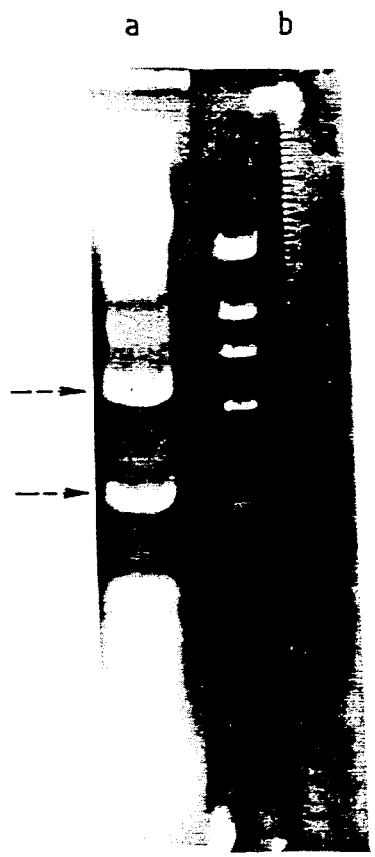
FIG. 4 is a photograph of electrophoretic migration patterns of bacterial cell constituents subjected to the instantly claimed process.

Bacteria containing the plasmid to be isolated, are cultivated in an LB medium (bactotryptone, bacto yeast extract and NaCl) containing an antibiotic, at 37° C. in the culture chamber 1, then said bacteria are transferred into the treatment tank 4 and the culture medium is removed by filtering by passage over the membrane 5, by operating the vacuum pump 6. The 1% agarose kept at 37° C. is run into the treatment tank 4; it is left to cool 15 minutes, in order that the agarose containing the bacteria may polymerise and the block obtained is incubated for 10 minutes at room temperature in a 6 mg/ml lysozyme solution. A proteinase K solution at 5 mg/ml and 10% sodium dodecyl sulfate is added and by employing heat regulating means, it is incubated for one hour at 42° C. The cells, thus treated, are ready for the electrophoretic migration which is carried out for three hours at 70 volts (about 60 mA); there are then obtained, the desired plasmids, as shown in FIG. 4 (arrows) at a and in FIG. 4 at b represents a size marker (lambda phage digested with HindIII).

EXAMPLE 2

Figure 5:
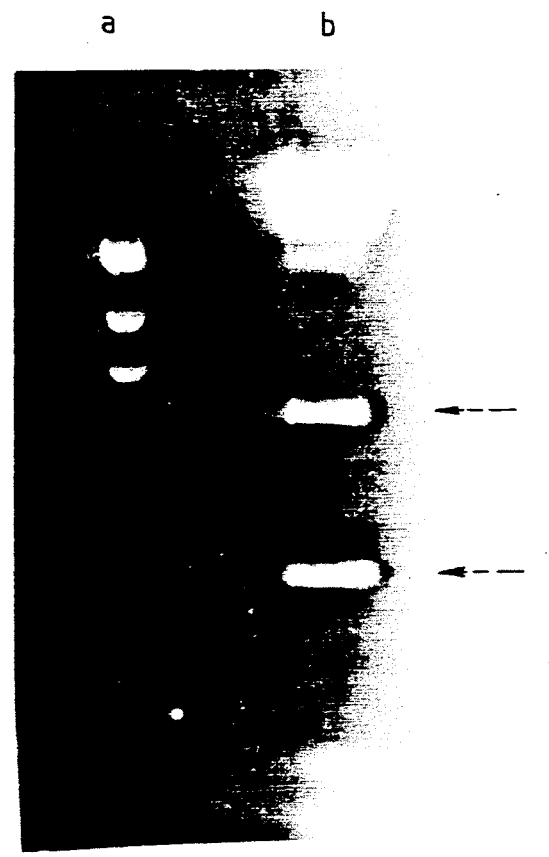
FIG. 5 is a photograph of electrophoretic migration patterns of bacterial cell constituents subjected to the instantly claimed process.

Procedure is as in Example 1, the migration being performed for twelve hours at 10 volts (about 9 mA); the desired plasmids are then obtained as shown b in FIG. 5 (arrows); the column a of FIG. 5 shows a size marker (lambda phage digested with HindIII).

Thus as emerges from the foregoing, the invention is in no way limited to those of its methods of practice, embodiments and uses which have been described more explicitly; it encompasses thereof on the contrary, all modifications which may come to the spirit of the technician in the art, without departing from the framework, or the scope of the present invention.

What is claimed is:

1. An apparatus for obtaining whole plasmids and cosmids present in bacterial cells comprising:
   (a) at least one lysis, solubilization and inclusion tank for lysing, solubilizing and including bacterial cells in an inclusion gel, the bottom of said at least one tank being in the form of a membrane having a porosity for the separation of molecules of molecular weight higher than 80 kDa for separating said bacterial cells from their culture medium, said at least one tank having four walls at least one, one of said four walls being removable and/or extractable;
   (b) a pump operably connected to said at least one tank for sucking and removing culture medium through said membrane;
   (c) a set of introduction means located in flow communication with said at least one tank for introducing lysis and solubilization reagents and hot inclusion gel to said at least one tank;
   (d) at least one electrophoresis gel, adjacent and in communication with said at least one tank; said at least one tank being placed in communication with said at least one electrophoresis gel by said removable and/or extractable wall placed in position between said at least one tank and said at least one electrophoresis gel, for the flow of the gel into said at least one tank; and
   (e) at least one means for applying an electric field across the at least one electrophoresis gel, causing electrophoretic migration of the bacterial cells.

2. The apparatus according to claim 1, wherein the means for applying an electric field comprises electrodes, and the three other walls of the at least one tank are fixed walls of which one, adjacent to one electrode of the means of applying the electric field, is a dialysis membrane.

3. The apparatus according to claim 1, wherein one of the three other walls of the at least one tank is removable and/or extractable.

4. The apparatus according to claim 1, wherein the three other walls of the at least one tank are simultaneously removable and/or extractable.

5. The apparatus according to claim 4, wherein the means for applying an electric field comprises electrodes, and the three other walls of the at least one tank are fixed walls of which one, adjacent to one electrode of the means of applying the electric field, a dialysis membrane.

6. The apparatus according to claim 1 further comprising a detector located adjacent said at least one electrophoresis gel for locating the site of the whole plasmids and cosmids electrophoresed out of the bacterial cells after said electrophoretic migration.

7. An apparatus for obtaining whole plasmids and cosmids present in bacterial cells comprising:
   (a) at least one cell culture chamber comprising a certain number of parallel compartments enabling the growth in parallel of different bacterial cells;
   (b) a set of transfer tubes for transferring said different bacterial cells from the parallel compartments of said culture at least one chamber to at least one lysis, solubilization and inclusion tank;
   (c) at least one lysis, solubilization and inclusion tank for lysing, solubilizing and including said different bacterial cells in an inclusion gel, the bottom of said at least one tank being in the form of a membrane having a porosity for the separation of molecules of molecular weight higher than 80 kDa for separating said different bacterial cells from their culture medium, said at least one tank having four walls;
   (d) an pump operably connected to said at least one tank for sucking and removing culture medium through said membrane;
   (e) a set of introduction means located in flow communication with said at least one tank for introducing lysis and solubilization reagents and the hot inclusion gel to said at least one tank;
   (f) at least one electrophoresis gel, adjacent and in communication with said at least one tank; said at least one tank being placed in communication with said at least one electrophoresis gel by said removable and/or extractable wall placed in position between said at least one tank and said at least one electrophoresis gel; and (g) at least one means for applying an electric field across the at least one electrophoresis gel, causing electrophoretic migration of the different bacterial cells.

8. The apparatus according to claim 7, wherein said pump is a peristaltic pump.

9. The apparatus according to claim 7, wherein said pump is an excess pressure generator.

10. The apparatus according to claim 7, wherein said pump is a vacuum pump connected to said at least one tank.

11. The apparatus of claim 7, wherein said pump is capable of simultaneously transferring the bacterial cells from said at least one cell culture chamber to said at least one tank and sucking and removing culture medium through the membrane, said pump being positioned downstream said membrane.

12. The apparatus according to claim 7 further comprising a detector located adjacent said at least one electrophoresis gel for locating the site of the whole plasmids and cosmids electrophoresed out of the different bacterial cells after said electrophoretic migration.

* * * * *

UNITED STATES PATENT AND TRADEMARK OFFICE
CERTIFICATE OF CORRECTION

PATENT NO. : 5,304,488
DATED : April 19, 1994
INVENTOR(S) : Daniel Cohen, Frederic Dufau and Jean Hache It is certified that error appears in the above-indentified patent and that said Letters Patent is hereby corrected as shown below:

Column 3, line 21, before "the" (first occurrence), insert —practicing—
Column 5, line 61, after "walls" delete "at least one"
Column 6, line 45, after "said" insert —at least one—
Column 6, line 45, after "culture" delete —at least one—
Column 6, line 68, after "gel" insert —for the flow of gel into said at least one tank—.

Signed and Sealed this

Sixth Day of December, 1994

Attest:

BRUCE LEHMAN

Attesting Officer

Commissioner of Patents and Trademarks